United States Patent [19]

Draper et al.

[11] Patent Number: 4,993,091
[45] Date of Patent: Feb. 19, 1991

[54] TANNING BED LINER ASSEMBLY

[75] Inventors: Beverly Draper; Gayle Parkevich, both of Cutler, Ind.

[73] Assignee: Tan Sense, Inc., Cutler, Ind.

[21] Appl. No.: 311,648

[22] Filed: Feb. 16, 1989

[51] Int. Cl.⁵ .............................................. A47G 9/02
[52] U.S. Cl. .......................................... 5/487; 5/488; 5/508; 128/376; 428/918
[58] Field of Search .................. 5/496, 498, 488, 487, 5/508, 417–420; 128/371–377; 428/913, 918

[56] References Cited

U.S. PATENT DOCUMENTS

| | | | |
|---|---|---|---|
| 1,891,629 | 12/1932 | Van Wagner | 5/488 |
| 1,967,422 | 7/1934 | Nadelson | 5/488 |
| 3,761,973 | 10/1973 | Leventhal | 5/499 |
| 4,025,973 | 5/1977 | Walbrecht | 5/488 |
| 4,118,438 | 10/1978 | Matsui et al. | 428/918 X |
| 4,335,724 | 6/1982 | Frei et al. | 128/373 |
| 4,358,865 | 11/1982 | Pagel et al. | 5/487 |
| 4,660,561 | 4/1987 | Nielsen | 128/376 |
| 4,663,787 | 5/1987 | Kölsch | 128/376 X |
| 4,683,887 | 8/1987 | Kramer et al. | 128/376 |
| 4,825,868 | 5/1989 | Susa et al. | 128/376 |

FOREIGN PATENT DOCUMENTS

| | | | |
|---|---|---|---|
| 214353 | 3/1987 | European Pat. Off. | 128/396 |
| 2910468 | 9/1980 | Fed. Rep. of Germany | 128/376 |
| 2911758 | 10/1980 | Fed. Rep. of Germany | 128/376 |
| 2406978 | 6/1979 | France | 5/494 |
| 2475400 | 8/1981 | France | 5/417 |
| 7809719 | 3/1980 | Netherlands | 128/376 |
| 6146 | 10/1987 | PCT Int'l Appl. | 128/396 |

OTHER PUBLICATIONS

Copy of an advertising circular for a SANITAN transparent covering.

Primary Examiner—Eric K. Nicholson
Attorney, Agent, or Firm—Barnes & Thornburg

[57] ABSTRACT

A liner assembly is provided for covering a support surface. The liner assembly includes a film sheet for covering the surface, the film sheet allowing rays to pass therethrough, and a dispenser for storing an unused portion of the film sheet to permit a user to dispense a section of the film sheet onto the surface prior to each use. The liner assembly ensures that the surface is in a clean and sanitary condition prior to each use.

27 Claims, 1 Drawing Sheet

TANNING BED LINER ASSEMBLY

BACKGROUND AND SUMMARY OF THE INVENTION

The present invention relates to a liner for covering a tanning bed during a tanning session More particularly, the present invention relates to a film sheet for covering a lower tanning surface of a tanning bed and a dispenser for storing an unused portion of the film sheet to permit a user to dispense a section of the film sheet onto the lower tanning surface prior to a tanning session.

Indoor tanning is becoming increasingly popular, especially during winter months when outdoor tanning is not possible. The use of indoor tanning beds permits a user to remain tan throughout the year, or to obtain a base tan in preparation for the summer outdoor tanning season.

In conventional tanning bed assemblies, the tanning bed includes a lower tanning surface to support the user's body during a tanning session. The lower tanning surface is generally formed from plexiglass or other suitable material that transmits ultraviolet light to the user from bulbs located under the lower tanning surface.

After the user is positioned on the lower tanning surface, an upper portion of the tanning bed pivots downward so that an upper tanning surface is situated over the user. This configuration surrounds the user with the ultraviolet light bulbs and permits the user to obtain a full-body tan without rotating his or her body.

During a tanning session, natural body oils and perspiration from the user can collect on the lower tanning surface. In addition, sun tanning oils and lotions used during the tanning session can also build up on the lower tanning surface. Therefore, the tanning bed provides an excellent environment for the spread of transmittable diseases from one user to another.

Because of this health risk, it is necessary to take precautions to insure that the lower tanning surface is in a clean, sanitary condition prior to each tanning session. In conventional tanning bed assemblies, a suitable cleaning fluid is used to remove oil, lotion, and perspiration from the lower tanning surface after each tanning session.

After repeated cleanings with a cleaning fluid, the lower tanning surface can deteriorate or become scratched. Additionally, if abrasive cleansers are used, damage to the lower tanning surface occurs more rapidly. This causes the percent transmittance for ultraviolet light of the lower tanning surface to drop below acceptable levels which results in the need to replace the plexiglass surface. As will be understood, such replacement can be very expensive.

One object of the present invention is to provide a disposable liner to cover the lower tanning surface to provide a clean, sanitary surface for the user to lie on during a tanning session.

Another object of the present invention is to provide a dispenser that is economical and easy to use to permit a user to cover the tanning surface with the liner, thereby protecting the lower tanning surface and eliminating the need to clean the lower tanning surface after each tanning session.

According to the present invention, a liner assembly for use with a tanning bed includes a film sheet for covering a lower tanning surface of the tanning bed. The film sheet has a percent transmittance for ultraviolet light of at least 75 percent. The assembly also includes a dispenser for storing an unused portion of the film sheet to permit a user to remove a section of the unused portion to cover the lower tanning surface prior to each tanning session.

In a preferred embodiment of the present invention, the film sheet comprises a continuous sheet having a predetermined length. The film sheet is situated on a cylinder or tube to form a film sheet roll, and the dispenser includes means for permitting rotation of the tube inside the dispenser to permit a user to remove the film sheet from the dispenser.

The assembly also includes means for securing the section of the film sheet covering the lower tanning surface to an end portion of the tanning bed to hold the film sheet in a predetermined position over the lower tanning surface during a tanning session. The securing means may illustratively be a releasable magnetic catch, a pressure fit apparatus or any other suitable device for holding the film sheet in its predetermined position.

The film sheet is preferably made from a flexible material having a thickness suitable to prevent tearing or "bunching" as the film sheet is removed from the dispenser. In a preferred embodiment, the film sheet comprises a low density polyethylene material having a thickness of about 0.5 mil which is available from the Dow Chemical Company in Midland, Mich.

One feature of the present invention is the provision of means for storing and dispensing a disposable film sheet to cover a lower tanning surface of a tanning bed prior to a tanning session. Advantageously, such a feature minimizes the risk of transmitting diseases from one user to another due to contamination of the lower tanning surface. Lotion, oil, and perspiration from a user are contained on the film sheet, and the film sheet is removed and discarded after the tanning session. The film sheet protects the lower tanning surface and eliminates the need to clean the lower tanning surface with a cleaning solution after each tanning session. This beneficially extends the life of the lower tanning surface.

Another feature of the present invention is the provision of means for securing the section of the film sheet covering the lower tanning surface to an end portion of the tanning bed. Advantageously, such a feature insures that the film sheet will remain in its proper position over the lower tanning surface during the tanning session.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
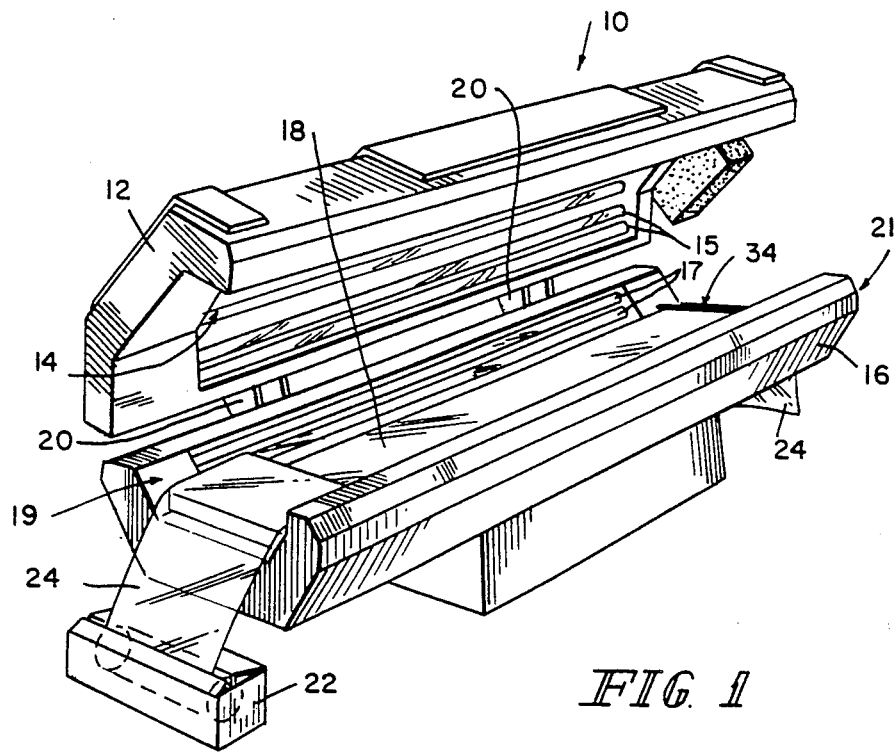
FIG. 1 is a perspective view of a preferred embodiment of the present invention showing a dispenser positioned at a first end of a tanning bed and a film sheet covering a lower tanning surface of the tanning bed.

As shown in FIG. 1, a conventional tanning bed assembly 10 includes an upper portion 12 having an upper tanning surface 14 and a lower portion 16 having a lower tanning surface 18. Upper and lower tanning surfaces 14, 18 are typically constructed from clear or translucent plexiglass or any other suitable material which permits substantially all of the ultraviolet light from a plurality of bulbs 15, 17 to pass through the upper and lower tanning surfaces 14, 18.

A user (not shown) lies flat on lower tanning surface 18 during a tanning session. Upper portion 14 then pivots on hinge members 20 to enclose the user inside the tanning booth assembly 10. Such a configuration surrounds the user's entire body with ultraviolet light bulbs 15, 17 so that the user can obtain a full-body tan without rotating his or her body.

During a tanning session, natural body oils and perspiration from the user, as well as a residue of sun tanning oils and lotion, can build up on lower tanning surface 18. This creates an environment conducive to the spread of transmittable diseases from one user to another. Therefore, in conventional tanning beds, it is normally necessary to clean the lower tanning surface 18 after each tanning session. Such repeated cleaning can cause the lower tanning surface 18 to become scratched, which can reduce significantly its percent transmittance of ultraviolet light. After the percent transmittance of lower tanning surface 18 falls below a certain predetermined level, it is necessary to install a new lower tanning surface 18. Replacing lower tanning surface 18 can be very expensive and can add significant costs to the operation of a tanning bed business.

To eliminate the need to clean the lower tanning surface 18 after each tanning session, a dispenser 22 is provided to dispense a film sheet 24 to cover lower tanning surface 18. Each user can unroll an unused portion of film sheet 24 to cover the lower tanning surface 18 before a tanning session. The unused film sheet 24 provides a clean, sanitary surface for the user to lie on, thereby reducing the risk of becoming infected from contaminants left on the lower tanning surface 18 by a prior user. After each tanning session, the soiled film sheet 24 is removed and replaced by a clean, unused section of film sheet 24.

The film sheet 24 has a percent transmittance for ultraviolet light of at least seventy-five percent (75%). Percent transmittance refers to that portion of the light which is transmitted by or passes through the film sheet 24.

Film sheet 24 may illustratively be a low density polyethylene film available from the Dow Chemical Company. The film may preferably have a thickness of 0.5 mil. However, it is understood that various types of materials having varying thicknesses can be used for the present invention as long as the minimum requirement of a 75% transmittance for ultraviolet light is maintained. Examples of materials that appear to be suitable are: oriented polypropylene; polystyrene; polyvinyl chloride; and polyvinylidene chloride.

Ultraviolet light includes an "A" portion (UVa) and a "B" portion (UVb) of the spectrum. UVa is the most important component of the ultraviolet light emitted by tanning bed bulbs 15, 17. The UVb portion is not as important and in most cases provides a very small component of the ultraviolet light emitted by tanning bed bulbs 15, 17. In a preferred embodiment of the present invention, film sheet 24 has a percent transmittance for UVa of about 88 percent and a percent transmittance for UVb of about 86 percent.

Figure 2:
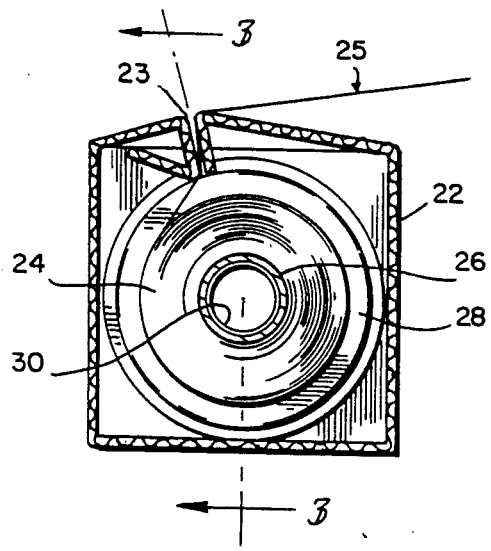
FIG. 2 is a transverse sectional view of the dispenser shown in FIG. 2.

FIG. 2 illustrates a sectional view of the dispenser 22 according to the present invention. The film sheet 24 is preferably wound around a cylinder or tube 26 for easy storage and dispensing capability. The tube 26 is situated inside dispenser 22. A loose end 25 of film sheet 24 passes through an aperture 23 formed in dispenser 22.

Figure 3:
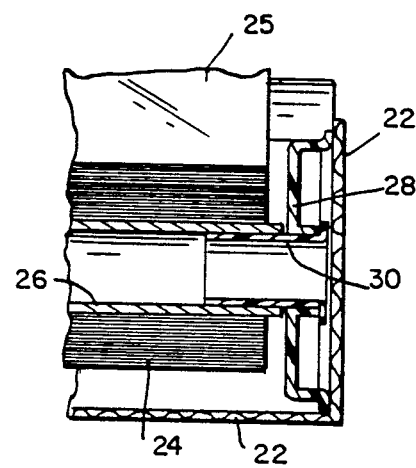
FIG. 3 is a partial sectional view taken along lines 3—3 of FIG. 2 illustrating an end portion of the dispenser.

As best shown in FIG. 3, dispenser 22 includes an end cap 28 having a central member or finger 30 which extends inside tube 26 to permit rotation of the tube 26 inside dispenser 22. By pulling on the loose end 25 of film sheet 24, a user can easily unroll a section of the film sheet 24 to cover the lower tanning surface 18 Film sheet 24 is preferably constructed from a film material thick enough to resist tearing and bunching as it is removed from dispenser 22 by the user, yet thin enough to permit at least 75 percent of the ultraviolet light to pass through film sheet 24.

As shown in FIG. 1, the dispenser 22 is located at a first end 19 of the tanning bed 10. Prior to a tanning session, a user removes a length of the unused portion of the film sheet 24 from dispenser 22 sufficient to cover lower tanning surface 18. A releasable magnetic catch 34 or other suitable means is provided for securing the section of the film sheet 24 covering lower tanning surface 18 to a second end portion 21 of the tanning bed 10. The magnetic catch 34 holds the film sheet 24 in a predetermined position over lower tanning surface 18 during a tanning session.

Dispenser 22 may illustratively be made of plastic, wood, aluminum, cardboard, or any suitable material. Various widths for the film sheet 24 are available to properly cover the various sizes of lower tanning surfaces 18 on different models of tanning beds 10 which are commercially available.

Although the invention has been described in detail with reference to a preferred embodiment, variations and modifications exist within the scope and spirit of the invention as described and defined in the following claims.

What is claimed is:

1. A liner assembly for use with an ultraviolet tanning bed, the assembly comprising
    a film sheet for covering a lower tanning surface of the tanning bed, the film sheet having a percent transmittance for ultraviolet light of at least 75 percent, and
    a dispenser for storing an unused portion of the film sheet to permit a user to remove a section of the unused portion to cover the lower tanning surface prior to each tanning session.

2. The liner assembly of claim 1, wherein the film sheet comprises a polymeric material.

3. The liner assembly of claim 2, wherein the film sheet has a thickness of about 0.5 mil.

4. The liner assembly of claim 1, wherein the film sheet comprises a polyethylene material.

5. The liner assembly of claim 4, wherein the film sheet comprises a low density polyethylene material.

6. The liner assembly of claim 5, wherein the film sheet has a thickness of about 0.5 mil.

7. The liner assembly of claim 1, wherein the film sheet is a continuous sheet having a predetermined length situated on a tube and the dispenser includes means for permitting rotation of the tube inside the dispenser to permit a user to remove a portion of the film sheet from the dispenser to be placed over the lower tanning surface.

8. The liner assembly of claim 7, wherein the means for permitting rotation of the tube inside the dispenser includes first and second end caps having a central portion extending into first and second ends of the tube to permit rotation of the tube.

9. The liner assembly of claim 1, further comprising means for securing the film sheet to an end portion of the tanning bed to hold the film sheet in a predetermined position over the lower tanning surface during a tanning session.

10. The liner assembly of claim 9, wherein the securing means includes a releasable magnetic catch for holding the film sheet on its predetermined position.

11. A liner assembly for use with a tanning bed, the assembly comprising
a disposable film sheet having a percent transmittance for ultraviolet light of at least 75 percent for covering a lower tanning surface of the tanning bed, an unused portion of the film sheet being situated on a cylinder to form a roll,
means for storing the roll of unused film sheet at a location separate from the tanning bed, and
means for permitting rotation of the film sheet roll inside the storing means to permit a user to dispense a section of the unused portion of the film sheet onto the lower tanning surface prior to a tanning session.

12. The liner assembly of claim 11, wherein the means for permitting rotation of the film sheet roll inside the storing means includes first and second end caps configured to engage first and second end portions of the cylinder to permit the cylinder to rotate.

13. The liner assembly of claim 11, further comprising means for securing the section of the film sheet covering the lower tanning surface to an end portion of the tanning bed to hold the film sheet in a predetermined position over the lower tanning surface during a tanning session.

14. The liner assembly of claim 13, wherein the securing means includes a releasable magnetic catch for holding the film sheet in its predetermined position on the lower tanning surface.

15. The liner assembly of claim 11, wherein the film sheet has a percent transmittance for ultraviolet light of at least 75 percent.

16. The liner assembly of claim 15, wherein the film sheet is made of a polymeric material.

17. The liner assembly of claim 16, wherein the film sheet has a thickness of about 0.5 mil.

18. The liner assembly of claim 15, wherein the film sheet comprises a polyethylene material 19. The liner assembly of claim 18, wherein the film sheet comprises a low density polyethylene material.

20. The liner assembly of claim 19, wherein the film sheet has a thickness of about 0.5 mil.

21. A liner assembly for covering a surface used to support a person, the assembly comprising
a film sheet for covering the surface, the film sheet having a percent transmittance for ultraviolet light of at least 75 percent for permitting the transmission of rays between the supported person and through the film sheet, and
a dispenser for storing an unused portion of the film sheet to permit a user to remove a section of the unused portion to cover the surface prior to each use.

22. The liner assembly of claim 21, wherein the film sheet comprises a polymeric material.

23. The liner assembly of claim 22, wherein the film sheet has a thickness of about 0.5 mil.

24. The liner assembly of claim 21, wherein the film sheet comprises a polyethylene material.

25. The liner assembly of claim 24, wherein the film sheet comprises a low density polyethylene material.

26. The liner assembly of claim 25, wherein the film sheet has a thickness of about 0.5 mil.

27. The liner assembly of claim 21, wherein the film sheet is a continuous sheet having a predetermined length situated on a tube and the dispenser includes means for permitting rotation of the tube inside the disperser to permit a user to remove a portion of the film sheet from the dispenser to be placed over the surface.

* * * * *